(12) United States Patent
Yang

(10) Patent No.: US 10,111,451 B2
(45) Date of Patent: Oct. 30, 2018

(54) FOOD, BEVERAGE OR PHARMACEUTICAL COMPOSITION CONTAINING FERMENTED EASTERN PRICKLY PEAR AND A PREPARATION METHOD THEREFOR

(71) Applicant: Mi Ran Yang, Seoul (KR)

(72) Inventor: Mi Ran Yang, Seoul (KR)

( * ) Notice: Subject to any disclaimer, the term of this patent is extended or adjusted under 35 U.S.C. 154(b) by 465 days.

(21) Appl. No.: 14/911,022

(22) PCT Filed: Aug. 11, 2014

(86) PCT No.: PCT/KR2014/007455
§ 371 (c)(1),
(2) Date: Feb. 8, 2016

(87) PCT Pub. No.: WO2015/020506
PCT Pub. Date: Feb. 12, 2015

(65) Prior Publication Data
US 2016/0199427 A1    Jul. 14, 2016

(30) Foreign Application Priority Data
Aug. 9, 2013 (KR) ........................ 10-2013-0094764

(51) Int. Cl.
| | | |
|---|---|---|
| *A61K 36/00* | (2006.01) | |
| *A23L 2/52* | (2006.01) | |
| *A23L 2/60* | (2006.01) | |
| *A23L 2/38* | (2006.01) | |
| *A61Q 19/00* | (2006.01) | |
| *A61K 8/97* | (2017.01) | |
| *A61K 36/33* | (2006.01) | |
| *A23L 33/105* | (2016.01) | |

(52) U.S. Cl.
CPC ................ *A23L 2/52* (2013.01); *A23L 2/382* (2013.01); *A23L 2/60* (2013.01); *A23L 33/105* (2016.08); *A61K 8/97* (2013.01); *A61K 36/33* (2013.01); *A61Q 19/00* (2013.01); *A23V 2002/00* (2013.01); *A61K 2800/85* (2013.01)

(58) Field of Classification Search
CPC ..................................................... A61K 36/00
USPC ....................................................... 424/725
See application file for complete search history.

(56) References Cited

U.S. PATENT DOCUMENTS

2011/0318432 A1    12/2011    Munafo et al.

FOREIGN PATENT DOCUMENTS

| | | |
|---|---|---|
| JP | S55-154916 A | 12/1980 |
| KR | 10-2006-0079053 A | 7/2006 |
| KR | 10-2009-0001401 A | 1/2009 |
| KR | 10-0961217 B1 | 6/2010 |
| KR | 10-2010-0135575 A | 12/2010 |
| KR | 10-1209380 B1 | 12/2012 |

OTHER PUBLICATIONS

Liang Ping et al., "Research on latic acid fermentation of opuntia juice beverage", G.X. Light Ind., Mar. 25, 2003, pp. 20-22.
Zhou Xinping, "Discussion on research and development of opuntia ficus-indica", Gansu Agriculture 2006, pp. 103-108, Issue 5.
International Search Report for International Patent Application No. PCT/KR2014/007455 filed Aug. 11, 2014.

*Primary Examiner* — Michael V Meller

(57) ABSTRACT

Provided is a food or drink composition for improving reflux esophagitis or skin diseases, containing fermented Eastern prickly pear.

1 Claim, No Drawings

FOOD, BEVERAGE OR PHARMACEUTICAL COMPOSITION CONTAINING FERMENTED EASTERN PRICKLY PEAR AND A PREPARATION METHOD THEREFOR

TECHNICAL FIELD

The present invention relates to a food or drink composition for improving reflux esophagitis or skin diseases, containing fermented Eastern prickly pear.

BACKGROUND ART

Since Eastern prickly pear, which belongs to the genus *Opuntia*, contains large amounts of various minerals such as calcium, magnesium, and the like, pectin ingredients, and the like, in addition to dietary fiber and vitamins, Eastern prickly pear is a nutritionally or pharmacologically excellent plant. As effects of Eastern prickly pear, an anti-inflammatory and analgesic effect and pulmonary tuberculosis alleviating effect were disclosed in "Dongeuibogam" (Korean traditional medical encyclopedia) and it was disclosed in Chinese traditional medicine dictionary that Eastern prickly pear had a function of improving a flow of Qi and blood circulation, lowering fevers, and detoxifying poisons. Further, as a diabetes therapeutic agent, a capsule and a tablet containing an ingredient of Eastern prickly pear were developed in Mexico.

Meanwhile, Eastern prickly pear as described above is ground as it is to thereby be drunk, or heated for a long period of time, and then extracted, such that an extract thereof is drunk. However, in a case of grinding Eastern prickly pear and eating the ground material of Eastern prickly pear as it is, nutritional ingredients are not destroyed, which is nutritionally preferable. However, there is an offensive smell due to a terpene ingredient, such that it is a little difficult to eat Eastern prickly pear. Further, in the extract prepared by heating Eastern prickly pear at a high temperature, a relatively large amount of the nutritional ingredients is destroyed due to heating treatment for a long period of time, and as Eastern prickly pear is exposed to heat over the long period of time, a unique flavor, taste, color, or the like, thereof is changed, and freshness thereof is deteriorated, such that preference therefor may be rather deteriorated.

A preparation method of a drink containing Eastern prickly pear, which is characterized by adding pectin degrading enzyme and starch degrading enzyme in order to extract active ingredients of Eastern prickly pear, has been disclosed in Korean Patent Laid-Open Publication No. 10-2008-0103748, but the pectin degrading enzyme and starch degrading enzyme are used simply to soften the flesh of the Eastern prickly pear, and does not actually change the physical properties of Eastern prickly pear itself.

In addition, a composition for preventing or treating uterine cervical cancer, containing an organic solvent extract of Eastern prickly pear has been disclosed in Korean Patent Laid-Open Publication No. 10-2012-0004260.

Various physiological activities of Eastern prickly pear as described above have been known, but an effect on reflux esophagitis or skin diseases is not yet known. Particularly, an effect of fermented Eastern prickly pear obtained by fermenting Eastern prickly pear is also not known.

RELATED ART DOCUMENT

Patent Document (Patent Document 1) Korean Patent Laid-Open Publication No. 2008-0103748

(Patent Document 2) Korean Patent Laid-Open Publication No. 2012-0004260

Non-Patent Document (Non-Patent Document) Not exist

DISCLOSURE

Technical Problem

The present invention provides a novel herbal composition of which safety is verified because it is not toxic to the human body while having excellent effects of treating, preventing, or alleviating reflux esophagitis or skin diseases.

In addition, the present invention provides a processed Eastern prickly pear product in which activities such as an anti-oxidant activity, an anti-inflammatory activity, and the like, of Eastern prickly pear are improved.

Further, the present invention provides therapeutic uses of fermented Eastern prickly pear.

Technical Solution

The present inventors found that fermented Eastern prickly pear or a composition containing the same is effective in improving reflux esophagitis or skin diseases, thereby completing the present invention.

According to an exemplary embodiment of the present invention, there is provided a pharmaceutical composition for treating reflux esophagitis or skin diseases, containing fermented Eastern prickly pear.

According to another exemplary embodiment of the present invention, there is provided a food or drink composition for treating reflux esophagitis or skin diseases, containing fermented Eastern prickly pear.

According to another exemplary embodiment of the present invention, there is provided a preparation method of fermented Eastern prickly pear.

Advantageous Effects

A pharmaceutical composition or food composition according to the present invention may be effective in improving reflux esophagitis or skin diseases, particularly, acne, or atopic dermatitis.

Further, pharmaceutical composition or food composition according to the present invention may be significantly effective in treating or improving reflux esophagitis or skin diseases through a simple process of fermenting Eastern prickly pear, which is a natural material, without adding a separate synthetic additive or physiologically active material.

BEST MODE

The present invention provides a pharmaceutical composition for treating, preventing or alleviating reflux esophagitis or skin diseases, containing fermented Eastern prickly pear.

In addition, the present invention provides a food or drink composition for treating, preventing or alleviating reflux esophagitis or skin diseases, containing fermented Eastern prickly pear.

In the present invention, the fermented Eastern prickly pear means a material obtained by fermenting Eastern prickly pear itself, an extract of Eastern prickly pear, a ground material of Eastern prickly pear, or the like, using nuruk (Korean rice-wine starter) or *Aspergillus oryzae*. Further, the fermented Eastern prickly pear includes a purified material obtained by purifying a fermented product, a material obtained by removing nuruk or *Aspergillus oryzae* from the fermented product, or a filtrate of the fermented product, as well as the fermented product itself obtained through fermentation using nuruk or *Aspergillus oryzae*. In more detail, the fermented Eastern prickly pear may be a fermented product produced by adding nuruk or *Aspergillus oryzae* to the ground material of Eastern prickly pear and performing fermentation at 15° C. to 30° C. for 1 to 7 days.

In the present invention, a site of Eastern prickly pear to be used is not particularly limited, but a fruit (the remaining fruit flesh after separating a seed from the fruit), a seed, a stem, and a root thereof may be used. Therefore, a case of using Eastern prickly pear itself means a case of using the fruit (the remaining fruit flesh after separating the seed from the fruit), the seed, the stem, and the root thereof without grinding after harvesting and washing the fruit (the remaining fruit flesh after separating the seed from the fruit), the seed, the stem, and the root thereof. In a case of using the extract of Eastern prickly pear, an extraction solvent may be water, an organic solvent, or a mixture thereof. In a case of using the ground material of Eastern prickly pear, Eastern prickly pear ground to a size of 0.01 to 5 cm, more specifically, 0.2 to 3 cm, may be used. In addition, a material obtained by adding water, an organic solvent, or a mixture thereof to the ground material may be used.

The present inventors found that the fermented Eastern prickly pear obtained by fermenting Eastern prickly pear using nuruk or *Aspergillus oryzae* was significantly effective in treating reflux esophagitis or skin diseases while studying a method of enhancing a medicinal effect of Eastern prickly pear and a novel effect of Eastern prickly pear, thereby completing the present invention.

Therefore, an aspect of the present invention relates to a method of enhancing an anti-oxidant, anti-inflammatory, anti-bacterial, or anti-cancer activity of Eastern prickly pear by fermenting Eastern prickly pear using nuruk or *Aspergillus oryzae*. Further, another aspect of the present invention relates to fermented Eastern prickly pear of which an anti-oxidant, anti-inflammatory, anti-bacterial, or anti-cancer activity is enhanced, or a food or pharmaceutical composition containing the same.

The food, drink or pharmaceutical composition for treating reflux esophagitis or skin diseases, containing fermented Eastern prickly pear according to an exemplary embodiment of the present invention may further contain a sweetener in addition to Eastern prickly pear. The sweetener may be contained in order to assist fermentation of Eastern prickly pear and decrease a peculiar flavor of Eastern prickly pear. Examples of the sweetener may include sugars such as sugar, red sugar, brown sugar, glucose, fructose, sucrose, and the like, sugar alcohols such as mannitol, sorbitol, xylitol, and the like, synthetic sweeteners such as sodium cyclamate, sodium saccharin, aspartame, sucralose, acesulfame potassium, stevia, and the like, glycyrrhizin and salts thereof, honey, and the like. Preferably, white sugar, red sugar, or brown sugar may be used. Most preferably, red sugar or brown sugar may be used. A content of the sweetener may be 0.001 to 50 wt % based on a total weight of the pharmaceutical, food, or drink composition. In detail, the content may be 0.01 to 30 wt %.

The food, drink or pharmaceutical composition for treating, preventing, or alleviating reflux esophagitis or skin diseases according to an exemplary embodiment of the present invention may contain purified water, an excipient, and/or an additive. Examples of the additive may include a preservative, an acidulant, a flavoring agent, a corrigent, a thickening agent, a pH adjusting agent, or the like. Specific examples of the preservative may include alkylparabens such as methylparaben, propylparaben, and the like, benzoic acids such as sodium benzoate, and the like. Specific examples of the acidulant may include citric acid, ascorbic acid, malic acid, and the like. Examples of the flavoring agent may include menthol, camphor, refined oils such as peppermint oil, mint oil, cinnamon oil, and the like, orange flavor, drink flavor, and the like. Examples of the corrigent may include aminoacetic acid, refined oils such as lemon oil, orange oil, and the like, Examples of the thickening agent may include polyvinyl pyrrolidone, sodium alginate, chondroitin sodium sulfate, agar powder, gelatin, guar gum, xanthan gum, and the like. Examples of the pH adjusting agent may include acidic materials such as citric acid, lactic acid, malic acid, tartaric acid, adipic acid, and salts thereof.

In addition, the drink or food according to the present invention may further contain other ingredients known in the art for treating reflux esophagitis or skin diseases. For example, as other ingredients, there are antacids, gastric mucosal defense factor enhancers, digestive tract active agents, vitamins, crude drugs, stomachics, and the like. Specific examples of the antacid may include lansoprazole, rabeprazole sodium, omeprazole, scopolia extracts, *belladonna* extracts, isopropamide iodide, scopolamine hydrobromide, oxyphencyclimine hydrochloride, dicyclomine hydrochloride, and the like. Examples of the gastric mucosal defense factor enhancer include sucralfate, ecabet sodium, cetraxate hydrochloride, benexate hydrochloride betadex, polarprezinc, and irsogladine maleate, and examples of the gastric tract active agent may include trimebutine maleate, mosapride citrate, cisapride, itopride hydrochloride, and the like. Examples of the vitamins may include vitamins $B_1$, $B_2$, and C, derivatives thereof, and salts thereof, vitamin E, vitamin D, and the like, and examples of the crude drug may include *Mallotus japonicus, Corydalis remota, Glycyrrhiza uralensis* Fischer, aloe, *Foeniculum vulgare, Isodon japonicus* Hara, *Gentiana scabra*, cinnamon, Perillae semen, *Aurantii Pericarpium, Panax ginseng*, hop, Strychni semen, and the like. Examples of the stomachics may include carnitine chloride, bethanechol chloride, betaine hydrochloride, glutamic acid hydrochloride, and the like.

The fermented Eastern prickly pear may be contained in the pharmaceutical, food, or drink composition according to the present invention at a content of 0.01 wt % to 80 wt % based on the entire composition.

In a case of using the fermented Eastern prickly pear as food or drink, the content of the fermented Eastern prickly pear may be, for example, 0.01 to 60 wt %.

A preparation method of fermented Eastern prickly pear according to an exemplary embodiment of the present invention may include:

adding nuruk or *Aspergillus oryzae* to Eastern prickly pear itself, an extract of Eastern prickly pear, or a ground material of Eastern prickly pear and performing fermentation.

A preparation method of fermented Eastern prickly pear according to another exemplary embodiment of the present invention may include:

adding a sweetener to Eastern prickly pear itself, an extract of Eastern prickly pear, or a ground material of Eastern prickly pear; and adding nuruk or *Aspergillus oryzae* to the Eastern prickly pear itself, the extract of Eastern prickly pear, or the ground material of Eastern prickly pear to which the sweetener is added, and performing fermentation.

In the adding of the sweetener, an addition amount of the sweetener may be 0.1 to 10 times, more specifically, 0.5 to 5 times a volume of the Eastern prickly pear itself, the extract of Eastern prickly pear, or the ground material of Eastern prickly pear. In more detail, the addition amount of the sweetener may be about 1 time of the volume of the Eastern prickly pear itself, the extract of Eastern prickly pear, or the ground material of Eastern prickly pear. When the content is within the above-mentioned range, fermentation using the nuruk or *Aspergillus oryzae* may be effectively performed.

The preparation method may further include, after adding the sweetener, aging the Eastern prickly pear at room temperature for 5 to 30 days. In spite of the viscosity of Eastern prickly pear, the sweetener may be deeply infiltrated into Eastern prickly pear by aging.

In the case of using Eastern prickly pear itself in the present invention, a fruit (the remaining fruit flesh after separating a seed from the fruit), a seed, a stem, or a root itself of Eastern prickly pear may be used.

In the case of using the extract of Eastern prickly pear in the present invention, the extract may be obtained by extracting the fruit (the remaining fruit flesh after separating a seed from the fruit), the seed, the stem, or the root of Eastern prickly pear with water, an organic solvent, or a mixture thereof. An extraction temperature is 15° C. to 30° C., and an extraction time is 24 to 80 hours, but the extraction time may be changed depending on a size of Eastern prickly pear. Water or the organic solvent may be additionally removed by a drying and concentrating step after extraction. In a case of using the ground material of Eastern prickly pear, a material obtained by grinding Eastern prickly pear at a size of 0.01 to 5 cm, more specifically, 0.2 to 3 cm, and adding water, an organic solvent, or a mixture thereof to the ground material may be used. Alternatively, a material obtained by adding water, the organic solvent, or the mixture thereof to Eastern prickly pear and grinding them at once may be used.

The nuruk or *Aspergillus oryzae* may be added at a content of 10 to 30 vol %, more specifically, 16 to 25 vol % based on a volume of the Eastern prickly pear itself, the extract of Eastern prickly pear, or the ground material of Eastern prickly pear to which the sweetener is added. In a case in which the content of the nuruk or *Aspergillus oryzae* is within the above-mentioned range, fermentation using the nuruk may be effectively performed. Most preferably, about 20 vol % of the nuruk or *Aspergillus oryzae* may be used. The preparation method may further include, after adding of the nuruk or *Aspergillus oryzae*, uniformly stirring or mixing a mixture. In the case in which the stirring or mixing is added, a fermentation reaction may be performed without a large deviation depending on a part or site.

The performing of the fermentation may include obtaining a fermented Eastern prickly pear solution by maintaining the Eastern prickly pear itself, the extract of Eastern prickly pear, or the ground material of Eastern prickly pear to which the nuruk or *Aspergillus oryzae* is added in a fermenter at 15° C. to 30° C. for 1 to 7 days. The performing of the fermentation may be performed by additionally adding water. A fermentation temperature may be preferably 20° C. to 25° C., and a fermentation time may be preferably 2 to 5 days, most preferably, 3 days. An addition amount of water may be 500 mL to 10 L, specifically, 1 L to 8 L, and more specifically, 4 L to 6 L, per 1 kg of the Eastern prickly pear itself, the extract of Eastern prickly pear, or the ground material of Eastern prickly pear to which the nuruk or *Aspergillus oryzae* is added. The added water may be tap water, purified water, or drinking water, but preferably, the added water may be drinking water. More preferably, underground water may be used. The fermenter may be a sealed vessel or open vessel, but preferably, the fermenter may be the open vessel. More preferably, the fermenter may be an open vessel including a net.

In the present invention, the performing of the fermentation includes separately fermenting the fruit (the remaining fruit flesh after separating a seed from the fruit), the seed, the stem, or the root of Eastern prickly pear, respectively, or simultaneously fermenting them.

A composition containing fermented Eastern prickly pear, prepared as described above is effective in treating reflux esophagitis or skin diseases.

The fermented Eastern prickly pear according to the present invention may be provided as liquid-type fermented Eastern prickly pear or powder-type fermented Eastern prickly pear.

Therefore, in the preparation method of fermented Eastern prickly pear according to the present invention may further include powdering the prepared fermented Eastern prickly pear solution. As an example of a powdering process, powder of the fermented Eastern prickly pear solution may be prepared through a general freeze-drying process.

According to an exemplary embodiment, there is provided a preparation method of a drink composition containing fermented Eastern prickly pear, including:

adding a sweetener to Eastern prickly pear itself, an extract of Eastern prickly pear, or a ground material of Eastern prickly pear;

adding nuruk or *Aspergillus oryzae* to the Eastern prickly pear itself, an extract of Eastern prickly pear, or ground material of Eastern prickly pear to which the sweetener is added, and performing fermentation; and adding a drink additive to the fermented Eastern prickly pear.

According to another exemplary embodiment, there is provided a preparation method of a pharmaceutical composition containing fermented Eastern prickly pear, including:

adding a sweetener to Eastern prickly pear itself, an extract of Eastern prickly pear, or a ground material of Eastern prickly pear;

adding nuruk or *Aspergillus oryzae* to the Eastern prickly pear itself, the extract of Eastern prickly pear, or the ground material of Eastern prickly pear to which the sweetener is added, and performing fermentation; and adding a pharmaceutical excipient to the fermented Eastern prickly pear.

According to another exemplary embodiment, there is provided a preparation method of a drink composition containing fermented Eastern prickly pear, including:

adding a sweetener to Eastern prickly pear itself, an extract of Eastern prickly pear, or a ground material of Eastern prickly pear;

adding nuruk or *Aspergillus oryzae* to the Eastern prickly pear itself, the extract of Eastern prickly pear, or the ground material of Eastern prickly pear to which the sweetener is added, and performing fermentation; and adding water and alcohol to the fermented Eastern prickly pear and aging the fermented Eastern prickly pear; and heating the aged fermented Eastern prickly pear to remove alcohol.

The adding of the water and alcohol includes adding water or alcohol at a content corresponding to 1 to 10 times a content of the fermented Eastern prickly pear. The aging includes storing the fermented Eastern prickly pear at 15° C. to 30° C. for 1 to 10 days. In detail, the aging includes storing the fermented Eastern prickly pear at 15° C. to 18° C. for 2 to 5 days. The removing of the alcohol may include maintaining the aged fermented Eastern prickly pear at 60° C. to 80° C. for 1 to 10 hours. In this case, medicinal herb wine may be prepared by collecting vaporized alcohol.

The preparation method may further include after the removing of the alcohol, boiling the fermented Eastern prickly pear at 100° C. Further, the preparation method may further include filtering the fermented Eastern prickly pear through a filter. Various filtering methods may be used in the present invention, but in order to minimize a loss of nutrients and a change in ingredients of the fermented Eastern prickly pear, only residues such as a thorn, a peel, a seed, a root, and the like, of Eastern prickly pear that are not fermented, may be filtered.

The pharmaceutical composition according to the present invention may be prepared in various formulations for suitable administration purpose. Examples of a suitable formulation may include all formulations generally used in a drug for systemic administration drug. It is preferable that the pharmaceutical composition has a unit formulation particularly suitable for oral administration or parenteral injection. In a case in which the composition is a liquid formulation for oral administration such as a suspension, a syrup, an elixir, an emulsion, and a solution, a useful pharmaceutical medium such as water, glycol, oil, alcohol or the like may be used. Alternatively, in a case in which the composition is a powder, pill, capsule, or tablet formation, useful pharmaceutical mediums such as a solid carrier, for example, starch, sugar, kaolin, a diluent, a lubricant, a binder, a disintegrant, or the like, may be used. Since the tablet or capsule may be easily administered, the tablet or capsule may be the most advantageous unit formulation for oral administration. In this case, a solid pharmaceutical carrier may be used. In a case of a composition for parenteral administration, a carrier may include another ingredient, for example, an ingredient assisting in dissolution, but generally, the composition may contain water. In a case of suspension, the suspension may also be prepared using a suitable liquid carrier, a suspending agent, or the like. In addition, the formulation may include a solid formulation capable of being directly converted into a liquid formulation immediately before being used.

Particularly, it is advantageous to formulate the pharmaceutical composition as described above in a dosage unit form for easiness of administration and uniformity of administration dose. As used herein, the term "dosage unit form" may mean a form in which a physically segregated unit suitable for a unit dose is used, and each dosage unit contains a predetermined content of active ingredients calculated so as to obtain a desired therapeutic effect in relation to a pharmaceutical carrier to be required. Examples of the administration unit form as described above may include tablet (including a scored or coated tablet), capsules, pills, powders, packets, wafers, suppositories, injection solutions or suspensions, or the like, and segregated multiples. Most preferably, the above-mentioned pharmaceutical composition may be formulated in a form of tablets, capsules, solutions, or suspensions for easiness of rapid administration.

An administration dose of the pharmaceutical, food, or drink composition according to the present invention may be suitably determined and changed depending on age, weight, and a state of a patient to be treated, a specific formulation, an administration route and purpose. A daily dose of the extract of Eastern prickly pear or a freeze-dried material of thereof used in the present invention in order to treat reflux esophagitis or skin diseases, is 1 mg to about 1000 mg, preferably, about 5 mg to about 700 mg, and more preferably, about 10 mg to about 500 mg based on a non-toxic administration level. Of course, the administration dose may be changed depending on various factors. Therefore, in some cases, an administration dose smaller than the above-mentioned administration dose may be sufficient, but in other cases, an administration dose larger than the above-mentioned administration dose may be required.

The pharmaceutical composition according to the present invention may be orally administered as it is, or be added to selected food or drink such as alcoholic drink or tea, to thereby be administered.

The fermented Eastern prickly pear may be used as a raw material of a food or drink suppressing reflux esophagitis or skin diseases. The fermented Eastern prickly pear according to the present invention, added to the drink or food may be in a liquid state. The drink or food composition containing fermented Eastern prickly pear according to the present invention may be processed using a processing method including methods generally used for cooking, processing, or preparing the drink or food as long as the drink or food composition contains the fermented Eastern prickly pear as the active ingredient. The drink or food according to the present invention may be concentrated. As long as the fermented Eastern prickly pear is contained at a content required in order to exhibit physiological functions of the drink or food, a shape of the drink or food is not limited. The food or drink according to the present invention may be in an ingestible form such as tablets, granules, and capsules. A concentrated drink or food provided in a concentrate form and used after being suitably diluted before intake may also be included in the drink or food according to the present invention.

In order to treat, prevent, or alleviate reflux esophagitis or skin diseases, 100 ml of the food or pharmaceutical composition containing 0.01 to 80 wt % of the extract of Eastern prickly pear based on 100 ml of the composition may be administered to an adult once a day or twice a day.

In the present invention, the pharmaceutical, food, or drink composition containing the extract of Eastern prickly pear may be administered to or ingested by a subject under fasting conditions. Preferably, the pharmaceutical, food, or drink composition may be administered or ingested before 30 minutes of a meal.

Hereinafter, the present invention will be described in more detail through Examples, but the following Examples are provided by way of examples of the present invention. Therefore, the present invention is not limited to the following Examples.

Preparation Example 1 Preparation of Fermented Eastern Prickly Pear

A fruit, a stem, and a root of Eastern prickly pear (at least 5 years old, purchased from Chang-am Eastern prickly pear farm (12-2, Chang-am-ri, Sinchang-myeon, Asan-si, Chungcheongnam-do, Korea)) were washed with water four times, dried, and ground at a size of 1 cm to 4 cm using a grinder.

Commercialized brown sugar was added to the ground material at a volume ratio of 1:1 and uniformly mixed with each other, such that the brown sugar crystals were dissolved to thereby be uniformly dispersed in Eastern prickly pear.

The resultant was aged at room temperature for 15 days, and nuruk (product name: Sansung Nuruk, purchased from 603, Geumseong-dong, Geumjeong-gu, Busan, Korea) was added to the aged Eastern prickly pear at a volume ratio of 5:1 (Eastern prickly pear:nuruk), followed by stirring. The mixture of Eastern prickly pear and the nuruk was put into a fermenter, and 5 L of water per 1 kg of the mixture was added thereto, followed by stirring. The mixture was maintained at 20° C. to 25° C. for 3 days in a state in which a cover of the fermenter was not closed but a net was covered. After 3 days, fermentation was performed for a total of 6 days while stirring the inside of the fermenter, thereby preparing fermented Eastern prickly pear.

Preparation Example 2 Preparation of Drink Composition Containing Fermented Eastern Prickly Pear A fruit, a stem, and a root of Eastern prickly pear (at least 5 years old, purchased from Chang-am Eastern prickly pear farm (12-2, Chang-am-ri, Sinchang-myeon, Asan-si, Chungcheongnam-do, Korea)) were washed with water four times, dried, and ground at a size of 1 cm to 4 cm using a grinder.

Commercialized brown sugar was added to the ground material at a volume ratio of 1:1 and uniformly mixed with each other, such that the brown sugar crystals were dissolved to thereby be uniformly dispersed in Eastern prickly pear.

The resultant was aged at room temperature for 15 days, and nuruk (product name: Sansung Nuruk, purchased from 603, Geumseong-dong, Geumjeong-gu, Busan, Korea) was added to the aged Eastern prickly pear at a volume ratio of 5:1 (Eastern prickly pear:nuruk), followed by stirring. The mixture of Eastern prickly pear and the nuruk was put into a fermenter, and 5 L of water per 1 kg of the mixture was added thereto, followed by stirring. The mixture was maintained at 20° C. to 25° C. for 3 days in a state in which a cover of the fermenter was not closed but a net was covered.

The prepared fermented Eastern prickly pear was mixed with water at a volume ratio of 1:8, and secondarily aged at room temperature for 4 days. The secondary aging includes covering the net on a vessel in a state in which a cover of the vessel was not closed.

Comparative Preparation Example 1 Preparation of Extract of Eastern Prickly Pear A fruit, a stem, and a root of Eastern prickly pear (at least 5 years old, purchased from Chang-am Eastern prickly pear farm (12-2, Chang-am-ri, Sinchang-myeon, Asan-si, Chungcheongnam-do, Korea)) were washed with water four times, dried, and ground at a size of 1 cm to 4 cm using a grinder. After the ground material was mixed with a purified water and ethanol mixed solvent at a volume ratio of 1:8, an extract of Eastern prickly pear was prepared by solvent extraction at 90° C. for 8 hours.

Example 1 Measurement of Effect of Fermented Eastern Prickly Pear on Reflux Esophagitis 1. Selection of Subject for Confirming Effect In order to confirm an effect on reflux esophagitis, reflux esophagitis patients were collected.

Collection criteria were 1) a person diagnosed with reflux esophagitis in a hospital, 2) a person without a history of a hepatic disease over the last 3 years, 3) a person at the age of 20 years or more to 55 years or less, 4) a person without a history of drug hypersensitivity.

The number of subjects was 14, and an average age thereof was 35. Among them, eight subjects were men, and six subjects were women.

The subjects were randomly divided into three groups, such that group 1 (control group) was composed of a total of 4 subjects (two women and two men), group 2, which was a group administered with the fermented Eastern prickly pear, was composed of a total of 5 subjects (two women and three men), and group 3, which was a group administered with the extract of Eastern prickly pear, was composed of a total of 5 subjects (two women and three men).

2. Administration Method

For a total of 14 days, a placebo was administered to group 1, 100 ml of the fermented Eastern prickly pear of Preparation Example 1 was administered to group 2 twice a day, and 100 ml of the extract of Eastern prickly pear of Comparative Preparation Example 1 was administered to group 3 twice a day in a fasting state (30 minutes before breakfast and dinner). During the administration time, administration of other therapeutic drugs for reflux esophagitis was stopped.

Symptoms of reflux esophagitis were divided into heartburn, acid belching, globus hystericus, sour stomach, and chest paint, and all of the subjects filled out questionnaires on a degree of each symptom before treatment: A: no symptom, b: mild symptom, C: moderate symptom, D: slightly severe symptom, E: significantly severe symptom.

TABLE 1

|  |  | Heartburn | Acid belching | Globus hystericus | Sour stomach | Chest pain |
|---|---|---|---|---|---|---|
| Group 1 | 1 | C | B | A | C | B |
|  | 2 | D | C | B | D | D |
|  | 3 | D | B | B | D | D |
|  | 4 | B | C | B | C | C |
| Group 2 | 5 | B | C | C | C | B |
|  | 6 | D | D | C | D | C |
|  | 7 | C | C | B | C | D |
|  | 8 | B | B | D | D | C |
|  | 9 | B | C | B | C | B |
| Group 3 | 10 | C | A | C | C | B |
|  | 11 | B | B | C | B | C |
|  | 12 | B | C | B | C | B |
|  | 13 | C | C | C | D | D |
|  | 14 | D | C | D | C | C |

After administration for a total of 14 days, symptoms of reflux esophagitis were divided into heartburn, acid belching, globus hystericus, sour stomach, and chest paint, and all of the subjects re-filled out questionnaires on a degree of each symptom: A: no symptom, b: mild symptom, C: moderate symptom, D: slightly severe symptom, E: significantly severe symptom. The results were illustrated in the following Table 2.

TABLE 2

|  |  | Heartburn | Acid belching | Globus hystericus | Sour stomach | Chest pain |
|---|---|---|---|---|---|---|
| Group 1 | 1 | B | B | A | D | B |
|  | 2 | E | B | B | E | D |
|  | 3 | D | C | B | E | D |
|  | 4 | C | C | A | C | C |
| Group 2 | 5 | A | B | A | A | A |
|  | 6 | B | A | A | B | B |
|  | 7 | A | A | A | B | A |

TABLE 2-continued

|         |    | Heartburn | Acid belching | Globus hystericus | Sour stomach | Chest pain |
|---------|----|-----------|---------------|-------------------|--------------|------------|
|         | 8  | A         | B             | B                 | C            | A          |
|         | 9  | B         | A             | B                 | B            | B          |
| Group 3 | 10 | C         | A             | B                 | B            | B          |
|         | 11 | B         | C             | B                 | B            | B          |
|         | 12 | B         | B             | B                 | C            | C          |
|         | 13 | D         | B             | C                 | C            | D          |
|         | 14 | C         | B             | C                 | C            | B          |

Referring to the results, it may be appreciated that in the group administered with the placebo, symptoms of reflux esophagitis were further aggravated or still remained, in the group administered with the extract of Eastern prickly pear, the symptoms were slightly alleviated, but in the group administered with the fermented Eastern prickly pear, all of the symptoms of reflux esophagitis were evaluated as A: no-symptom or B: mild symptom, such that the fermented Eastern prickly pear may effectively treat reflux esophagitis.

Example 2 Measurement of Effect of Eastern Prickly Pear on Skin Disease

1. Selection of Subject for Confirming Effect

In order to confirm an effect on skin diseases, subjects were collected depending on the kind of skin diseases.

Skin diseases of the subjects to be collected were 1) acne and 2) atopic dermatitis.

The number of subjects was a total of 25, and an average age thereof was 25. Among them, 12 subjects were men, and 13 subjects were women.

The subjects were divided into two groups: group 1 (13 subjects) of acne patients and group 2 (12 subjects) of atopic dermatitis patients, and each of the groups was divided into three sub-groups, respectively. In group 1, sub-group 1 (control group) was composed of a total of 4 subjects (two women and two men), sub-group 2, which was a group administered with the fermented Eastern prickly pear of Preparation Example 1, was composed of a total of 4 subjects (three women and one man), and sub-group 3, which was a group administered with the extract of Eastern prickly pear of Comparative Preparation Example 1, was composed of a total of 5 subjects (two women and three men). In Group 2, sub-group 1 (control group) was composed of a total of 4 subjects (two women and two men), sub-group 2, which was a group administered with the fermented Eastern prickly pear of Preparation Example 1, was composed of a total of 4 subjects (three men and one woman), and sub-group 3, which was a group administered with the extract of Eastern prickly pear of Comparative Preparation Example 1, was composed of a total of 4 subjects (two women and two men).

2. Administration Method

For a total of 14 days, a placebo was administered to sub-group 1 of group 1 and sub-group 1 of group 2, 100 ml of the extract of Eastern prickly pear of Preparation Example 1 was administered to sub-group 2 of group 1 and sub-group 2 of group 2 twice a day, and 100 ml of the extract of Eastern prickly pear of Comparative Preparation Example 1 was administered to sub-group 3 of group 1 and sub-group 3 of group 2 twice a day in a fasting state (30 minutes before breakfast and dinner). During the administration time, administration of other therapeutic drugs for skin diseases was stopped.

The following Table 3 illustrates results obtained by measuring the number of pimples in the face and the neck of the acne patients participating in the test before and after administration.

TABLE 3

| Group 1     |    | Before Administration | After Administration |
|-------------|----|----------------------|---------------------|
| Sub-group 1 | 1  | 20                   | 15                  |
|             | 2  | 40                   | 42                  |
|             | 3  | 35                   | 32                  |
|             | 4  | 27                   | 24                  |
| Sub-group 2 | 5  | 66                   | 19                  |
|             | 6  | 41                   | 10                  |
|             | 7  | 25                   | 15                  |
|             | 8  | 39                   | 9                   |
| Sub-group 3 | 9  | 25                   | 20                  |
|             | 10 | 35                   | 28                  |
|             | 11 | 54                   | 43                  |
|             | 12 | 12                   | 11                  |
|             | 13 | 29                   | 30                  |

Referring to the results of Table 3, in the group administered with the placebo, the number of pimples increased or maintained, but in the group administered with the fermented Eastern prickly pear, the number of pimples significantly decreased, and in the group administered with the extract of Eastern prickly pear, the number of pimples slightly decreased.

The following Table 4 illustrates results obtained by self-evaluating a degree of itchiness in the atopic dermatitis patients participating in the test before and after administration (A: no symptom, b: mild symptom, C: moderate symptom, D: slightly severe symptom, E: significantly severe symptom).

TABLE 4

| Group 2     |    | Before Administration | After Administration |
|-------------|----|----------------------|---------------------|
| Sub-group 1 | 1  | B                    | A                   |
|             | 2  | C                    | C                   |
|             | 3  | C                    | D                   |
|             | 4  | D                    | C                   |
| Sub-group 2 | 5  | C                    | A                   |
|             | 6  | B                    | B                   |
|             | 7  | D                    | A                   |
|             | 8  | D                    | A                   |
| Sub-group 3 | 9  | C                    | A                   |
|             | 10 | D                    | C                   |
|             | 11 | C                    | C                   |
|             | 12 | B                    | B                   |

The following Table 5 illustrates results obtained by measuring a site in which atopic symptoms appeared in the atopic dermatitis patients participating in the test before and after administration.

TABLE 5

| Group 2 | | Before Administration | | | | | After Administration | | | | |
|---|---|---|---|---|---|---|---|---|---|---|---|
| | | Face and Neck | Arm | Leg | Chest and Abdomen | Back | Face and Neck | Arm | Leg | Chest and Abdomen | Back |
| Subgroup 1 | 1 | o | o | o | x | x | o | o | x | x | x |
| | 2 | x | o | o | o | x | x | x | o | o | o |
| | 3 | o | o | o | o | o | o | x | o | o | o |
| | 4 | x | o | x | o | o | o | o | x | o | x |
| Subgroup 2 | 5 | o | x | o | o | x | x | x | x | x | o |
| | 6 | x | o | o | o | o | x | x | o | x | x |
| | 7 | x | x | o | o | o | x | x | x | x | x |
| | 8 | x | o | o | o | x | x | x | x | x | o |
| Subgroup 3 | 9 | o | x | o | o | o | o | o | x | o | x |
| | 10 | x | x | o | o | o | x | o | o | o | o |
| | 11 | o | x | o | o | o | o | x | o | o | x |
| | 12 | o | o | o | o | x | o | o | o | x | x | o: There were atopic symptoms in the corresponding site
x: There was no atopic symptom in the corresponding site As illustrated in Tables 4 and 5, it may be confirmed that the fermented Eastern prickly pear according to the present invention is effective in alleviating the atopic symptoms and treating atopic dermatitis.

The invention claimed is:

1. A method of treating acne or atopic dermatitis in a human in need thereof consisting essentially of administering to the human in need thereof a therapeutically effective amount of Eastern Prickly Pear which has been fermented with nuruk or *Aspergillis oryzae* to effectively treat the acne or atopic dermatitis in the human in need thereof.

* * * * *